United States Patent
Gong et al.

(10) Patent No.: US 7,348,322 B2
(45) Date of Patent: Mar. 25, 2008

(54) GLUCOCORTICOID RECEPTOR MODULATORS AS ANTIINFLAMMATORY AGENTS

(75) Inventors: Leyi Gong, San Mateo, CA (US); Counde O'Yang, Sunnyvale, CA (US); Yun-chou Tan, San Jose, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/636,037

(22) Filed: Dec. 8, 2006

(65) Prior Publication Data

US 2007/0135427 A1 Jun. 14, 2007

Related U.S. Application Data

(60) Provisional application No. 60/749,180, filed on Dec. 9, 2005.

(51) Int. Cl.
*C07D 265/02* (2006.01)
*C07D 261/20* (2006.01)
*A61K 31/538* (2006.01)
*A61K 31/421* (2006.01)

(52) U.S. Cl. .................. 514/230.5; 514/375; 514/378; 514/381; 514/621; 544/105; 548/230; 548/245; 548/253; 564/169

(58) Field of Classification Search ............. 514/230.5, 514/375, 378, 381, 621; 544/105; 548/230, 548/253, 245; 564/169
See application file for complete search history.

(56) References Cited

U.S. PATENT DOCUMENTS

| | | |
|---|---|---|
| 6,245,804 B1 | 6/2001 | Lehmann et al. |
| 6,323,199 B1 | 11/2001 | Lehmann et al. |
| 6,344,454 B1 | 2/2002 | Lehmann et al. |
| 6,380,207 B2 | 4/2002 | Coghlan et al. |
| 6,548,534 B2 * | 4/2003 | Lehmann et al. ........... 514/435 |
| 6,903,215 B2 | 6/2005 | Betageri et al. |
| 2002/0077356 A1 | 6/2002 | Jaroch et al. |
| 2004/0254249 A1 | 12/2004 | Jaroch et al. |

FOREIGN PATENT DOCUMENTS

WO WO 98/54159 A1 12/1998
WO WO 02/10143 A1 2/2002

OTHER PUBLICATIONS

Betageri, R., et. al., "Trifluoromethyl Group as a Pharmacophore: Effect of Replacing a $CF_3$ Group on Binding and Agonist Activity of a Glucocorticoid Receptor Ligand," *Bioorg. Med. Chem. Lett.* (2005) 15, pp. 4761-4769.
Barnes, P.J., "Anti-inflammatory actions of glucocorticoids: molecular mechanisms", *Clinical Science* (1998) 94, 557-572.
Schacke, H. et al., "Mechanisms involved in the side effects of glucocorticoids", *Pharmacology & Therapeutics* (2002) 96, 23-42.
Heck, S. et al., "A distinct modulating domain in glucorticoid receptor monomers in the repression of activity of the transcription factor AP-1", *EMBO J.*, 1994 vol. 13 (17) pp. 4087-4095.
Prakash, G.K.S. et al., "Perfluoroalkylation with Organosilicon Reagents", *Chem. Rev.* 1997, 97, pp. 757-786.
Ramalah, P. et al., "Direct Trifluoromethylation of a-Keto Esters to b,b,b-Trifluorolactic Acid Derivates Using Trifluoromethyltrimethylsilane", *Synlett*, 1991 (09), pp. 643-644.
Reichardt, H.M. et al., "DNA Binding of the Glucocorticoid Receptor is Not Essential for Survival", *Cell*, 1998 vol. 93, pp. 531-541.
Tronche, F. et al., "Genetic dissection of Glucocorticoid receptor function in mice", *Curr Opin Genet Dev.*, 1998, 8 (5) pp. 532-538.

* cited by examiner

*Primary Examiner*—Kahsay Habte
(74) *Attorney, Agent, or Firm*—David J. Chang

(57) ABSTRACT

The present invention relates to compounds of formula I:

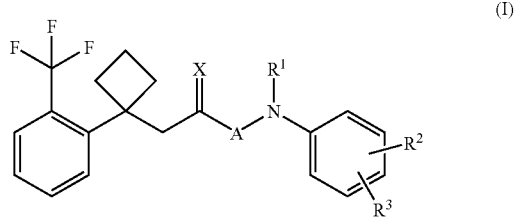

wherein A, X, $R^1$, $R^2$ and $R^3$ are as defined herein and pharmaceutically acceptable salts thereof. The invention also relates to methods of using the compounds of formula I and pharmaceutical compositions comprising the compounds of formula I.

13 Claims, No Drawings

GLUCOCORTICOID RECEPTOR MODULATORS AS ANTIINFLAMMATORY AGENTS

CROSS REFERENCE TO RELATED INVENTIONS

This application claims the benefit of priority of U.S. Provisional Patent Application Ser. No. 60/749,180 filed Dec. 9, 2005, which is incorporated herein by reference in its entirety.

FIELD OF THE INVENTION

This invention relates to oxime and propionamide compounds, and associated compositions and methods of use as therapeutic agents.

BACKGROUND OF THE INVENTION

Glucocorticoids provide effective treatment for inflammatory disease such as asthma and rheumatoid arthritis. However severe systemic side effects limit the dose that can be given and their long-term utility. The side effects include suppression of the hypothalamic-pituitary-adrenal (HPA) axis, osteoporosis, reduced bone growth in the young, behavioral alterations and disorders in lipid and glucose metabolism.

The glucocorticoid receptor (GR) is a member of a gene family known as the nuclear hormone receptors. After binding their cognate ligand, these receptors are activated and are capable of regulating transcription both positively and negatively. The detailed mechanism of this regulation, though not entirely understood, has become increasingly clear (R. M. Evans, Science, 1988, 240: 889-895; R. H. Oakley and J. Cidlowski, Glucocorticoids, N. J. Goulding and R. J. Flowers (eds), Boston: Birkhauser, 2001, 55-80). Glucocorticoids can freely diffuse across the plasma membranes into the cell where they bind to GR present within the cytoplasm. Once bound, a conformational change in the receptor causes the release of several chaperone proteins allowing the GR/ligand complex to translocate to the nucleus, dimerize and bind specifically and tightly to palindromic DNA sequences in the promoters of regulated genes. Hormone-bound receptor then recruits a group of proteins known as the coactivator complex. This complex is required to initiate transcription, and works by recruiting both the transcriptional machinery of the cell and histone acetyltransferases involved in opening the chromatin in the vicinity of the promoter. The transcription of a number of genes that contain GREs (glucocorticoid response elements) in their promoters is activated by GR. These include genes involved in gluconeogenesis, intermediary metabolism and the stress response.

In addition to transcriptional control exerted by GR at GREs, numerous genes, particularly those involved in the inflammation response, must be controlled through alternative mechanisms, since no GREs appear in the promoters of these genes. The promoters of numerous pro-inflammatory genes do contain binding sites for the transcription factors NF-KB and AP-1. It has been shown that the GR/ligand complex represses transcription of the pro-inflammatory genes by directly interacting with NF-kB or AP-1 and preventing transcriptional upregulation by the transcription factors (C. Jonat et al., Cell, 1990, 62: 1189-1204; H. F. Yang-Yen et al., Cell, 1990, 62: 1205-1215; A. Ray and K. E. Prefontaine, Proc. Natl. Acad. Sci. U.S.A., 1994, 91: 752-756). In vitro work with GR mutants incapable of DNA binding demonstrated that transrepression mediated by GR could be genetically dissociated from transactivation (S. Heck et al., EMBO J., 1994, 17: 4087-4095). This dissociation is further supported by a study where 'knock-in' transgenic mice were generated in which wild-type GR was substituted with a similar DNA binding domain mutant (H. M. Reichardt et al., Cell, 1998, 93: 531-541). These mice were incapable of regulating GRE-dependent GR target genes such as tyrosine amino transferase (TAT) or genes that are negatively regulated through interaction with a negative GRE, such as pro-opiomelanocortin (POMC). In contrast, these mice are capable of transrepressing genes activated by NF-kB or AP-1. Thus, the currently accepted model for corticosteroid control of inflammation predicts that GR, NFKB and AP-1 interact in a complex regulatory network leading to repression of cytokine expression.

According to this model a glucocorticoid modulator that would retain the transrepression activity and lose the transactivation activity would have fewer of the side effects associated with adrenal suppression, behavioral alterations, and gluconeogenesis. The anti-inflammatory affects would be retained.

SUMMARY OF THE INVENTION

The present invention relates to compounds of formula I:

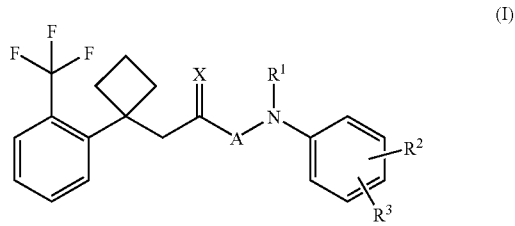

(I)

wherein A is $CH_2$ or C=O; $R^1$ is H or $C_1$-$C_6$ alkyl; $R^2$ and $R^3$ are each independently H, $CF_3$, $NO_2$ or an optionally substituted five-membered heteroaryl ring; or $R^2$ and $R^3$ together form a six-membered heterocyclyl ring substituted with 0-2 substituents selected from the group consisting of $C_1$-$C_6$ alkyl and oxo, with the proviso that when $R^2$ and $R^3$ together form an oxazolinyl ring, A is $CH_2$; X is O or N—$OR^4$, wherein $R^4$ is H or $C_1$-$C_6$ alkyl; and pharmaceutically acceptable salts thereof.

Another aspect of the invention relates to a method of treating an inflammatory disease through modulation of a glucocorticoid receptor comprising administering to a subject in need thereof a compound of formula I:

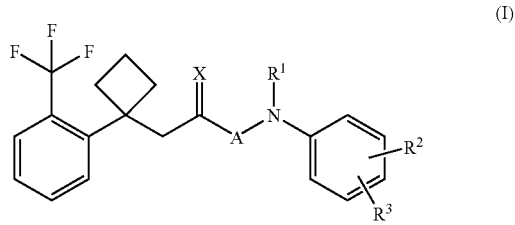

(I)

wherein A is $CH_2$ or C=O; $R^1$ is H or $C_1$-$C_6$ alkyl; $R^2$ and $R^3$ are each independently H, $CF_3$, $NO_2$ or an optionally substituted five-membered heteroaryl ring; or $R^2$ and $R^3$ together form a six-membered heterocyclyl ring substituted with 0-2 substituents selected from the group consisting of $C_1$-$C_6$ alkyl and oxo, with the proviso that when $R^2$ and $R^3$ together form an oxazolinyl ring, A is $CH_2$; X is O or N—$OR^4$, wherein $R^4$ is H or $C_1$-$C_6$ alkyl; and pharmaceutically acceptable salts thereof.

Another aspect of the invention is a pharmaceutical composition comprising an effective amount of a compound of Formula I;

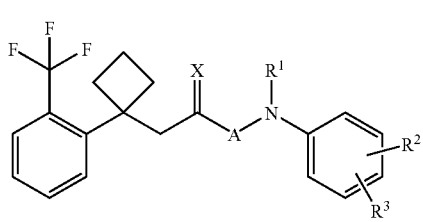

wherein:
A is $CH_2$ or C=O
$R^1$ is H or $C_1$-$C_6$ alkyl;
$R^2$ and $R^3$ are each independently H, $CF_3$, $NO_2$ or an optionally substituted five-membered heteroaryl ring; or $R^2$ and $R^3$ together form a six-membered heterocyclyl ring substituted with 0-2 substituents selected from the group consisting of $C_1$-$C_6$ alkyl and oxo, with the proviso that when $R^2$ and $R^3$ together form an oxazolinyl ring, A is $CH_2$;
X is O or N—$OR^4$, wherein $R^4$ is H or $C_1$-$C_6$ alkyl; and pharmaceutically acceptable salts thereof; and
a pharmaceutically acceptable excipient.

DETAILED DESCRIPTION OF THE INVENTION

All publications cited in this disclosure are incorporated herein by reference in their entirety.

Definitions:

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$ alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, tetrazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benz-imidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazol-idinyl, quinuclidinyl, quinolinyl, isoquinolinyl, benzimidazolyl, thiadiazolylidinyl, benzo-thiazolidinyl, benzoazolylidinyl, dihydrofuryl, tetrahydrofuryl, dihydropyranyl, tetra-hydropyranyl, thiamorpholinyl, thiamorpholinylsulfoxide, thiamorpholinylsulfone, dihydro-quinolinyl, dihydrisoquinolinyl, tetrahydroquinolinyl, tetrahydrisoquinolinyl, and the like.

"Optionally substituted", when used in association with "aryl", "phenyl", "heteroaryl" "cyclohexyl" or "heterocyclyl", means an aryl, phenyl, heteroaryl, cyclohexyl or heterocyclyl which is optionally substituted independently with one to four substituents, preferably one or two substituents selected from alkyl, cycloalkyl, cycloalkylalkyl, heteroalkyl, hydroxyalkyl, halo, nitro, oxo, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$-CONR$^a$R$^b$ (where n is an integer from 0 to 5, R' and R" are independently hydrogen or alkyl, and R and R$^b$ re, independently of each other, hydrogen, alkyl, cycloalkyl, cycloalkylalkyl, phenyl or phenylalkyl).

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuiric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulfiric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The term "modulate" means the ability of a molecule to alter the function of a target molecule by, for example, binding to and stimulating or inhibiting the target molecule's functional responses. "Modulator" means a molecule that interacts with and modulates a target molecule. The interactions include, but are not limited to, agonist, antagonist, and the like, as defined herein.

"Agonist" means a molecule that interacts with and enhances or increases the finction of a target molecule. As such, agonists include partial agonists and full agonists.

"Antagonist" means a molecule that directly or indirectly inhibits or suppresses the function of a target molecule. As such, antagonists include partial antagonists and full antagonists.

"Disease" and "Disease state" means any disease, condition, symptom, disorder or indication.

"Inflammatory disease" means disease states or indications that are accompanied by inflammatory, allergic, and/or proliferative processes and can include:

(i) Lung diseases: chronic, obstructive lung diseases of any genesis, particularly bronchial asthma and chronic obstructive pulmonary disease (COPD); adult respiratory distress syndrome (ARDS); bronchiectasis; bronchitis of various genesis; all forms of restrictive lung diseases, particularly allergic alveolitis; all forms of lung edema, particularly toxic lung edema; all forms of interstitial lung diseases of any genesis, e.g., radiation pneumonitis; and sarcoidosis and granulomatoses, particularly Boeck disease.

(ii) Rheumatic diseases or autoimmune diseases or joint diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); traumatic arthritis; collagenoses of any genesis, e. g., systemic lupus erythematosus, scleroderma, polymyositis, dermatomyositis, Sjogren syndrome, Still disease, and Felty syndrome;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vasculitis diseases: panarteritis nodosa, polyarteritis nodosa, arteritis temporalis, Wegner granulomatosis, giant cell arthritis, and erythema nodosum;

(v) Dermatological diseases: atopic dermatitis, particularly in children; psoriasis; pityriasis rubra pilaris; erythematous diseases triggered by various noxa, e.g., rays, chemicals, bums, etc.; bullous dermatoses; diseases of the lichenoid complex; pruritus (e.g., of allergic genesis); seborrheic dermatitis; rosacea; pemphigus vulgaris; erythema multiforme exudativum; balanitis; vulvitis; hair loss, such as occurs in alopecia areata; and cutaneous T cell lymphomas;

(vi) Renal diseases: nephrotic syndrome; and all types of nephritis, e.g., glomerulonephritis;

(vii) Hepatic diseases: acute liver cell disintegration; acute hepatitis of various genesis, e.g., viral, toxic, drug-induced; and chronically aggressive and/or chronically intermittent hepatitis;

(viii) Gastrointestinal diseases: inflammatory bowel diseases, e.g., regional enteritis (Crohn disease), colitis ulcerosa; gastritis; peptic esophagitis (refluxoesophagitis); and gastroenteritis of other genesis, e.g., nontropical sprue;

(ix) Proctological diseases: anal eczema; fissures; hemorrhoids; and idiopathic proctitis;

(x) Eye diseases: allergic keratitis, uveitis, or iritis; conjunctivitis; blepharitis; neuritis nervi optici; choroiditis; and sympathetic ophthalmia;

(xi) Diseases of the ear, nose, and throat (ENT) area: allergic rhinitis or hay fever; otitis extema, e.g., caused by contact eczema, infection, etc.; and otitis media;

(xii) Neurological diseases: brain edema, particularly tumor-related brain edema; multiple sclerosis; acute encephalomyelitis; meningitis; acute spinal cord injury; stroke; and various forms of seizures, e.g., nodding spasms;

(xiii) Blood diseases: acquired hemolytic anemia; and idiopathic thrombocytopenia;

(xiv) Tumor diseases: acute lymphatic leukemia; malignant lymphoma; lymphogranulomatoses; lymphosarcoma; extensive metastases, particularly in mammary, bronchial, and prostatic carcinoma;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Grave disease;

(xvi) Organ and tissue transplantations and graft-versus-host diseases;

(xvii) Severe states of shock, e.g., septic shock, anaphylactic shock, and systemic inflammatory response syndrome (SIRS);

(xviii) Substitution therapy in: congenital primary adrenal insufficiency, e.g., adrenogenital syndrome; acquired primary adrenal insufficiency, e.g., Addison disease, autoimmune adrenalitis, post-infection, tumors, metastases, etc.; congenital secondary adrenal insufficiency, e.g., congenital hypopituitarism; and acquired secondary adrenal insufficiency, e.g., post-infection, tumors, metastases, etc.;

(xix) Pain of inflammatory genesis, e.g., lumbago; and (xx) various other disease-states or conditions including type I diabetes (insulin- dependent diabetes), osteoarthritis, Guillain-Barre syndrome, restenosis following percutaneous transluminal coronary angioplasty, Alzheimer disease, acute and chronic pain, atherosclerosis, reperfusion injury, bone resorption diseases, congestive heart failure, myocardial infarction, thermal injury, multiple organ injury secondary to trauma, acute purulent meningitis, necrotizing enterocolitis and syndromes associated with hemodialysis, leukopheresis, and granulocyte transfusion.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state , i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Compounds of Formula (I) wherein A is $CH_2$ may be prepared by the method set forth in Scheme 1.

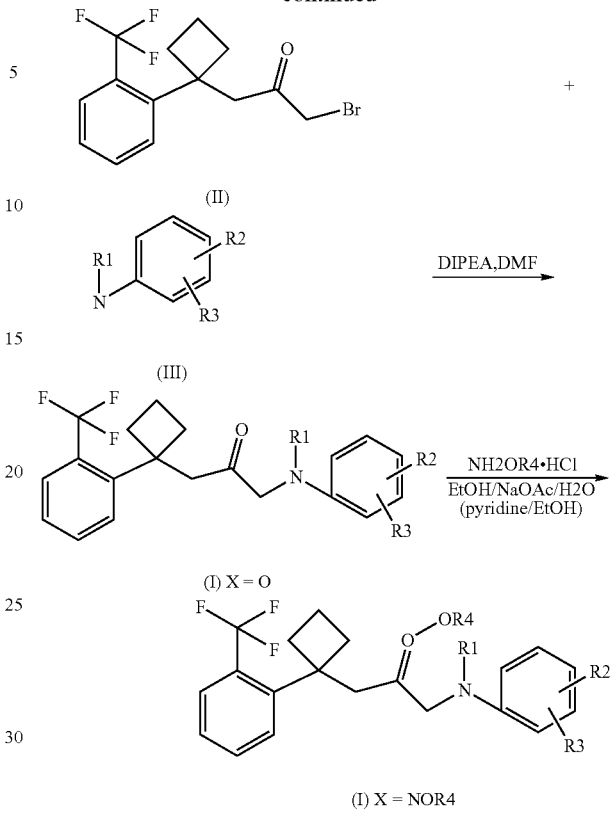

The intermediate, 1-bromo-3-[1-(2-trifluorometholy-phenyl)-cyclobutyl]-propan-2-one, of Formula (II) can be prepared using the starting materials, 1-bromo-2-trifluromethyl-benzene and 1-cyclobutylidene-propan-2-one. Reaction of the intermediate compound of Formula (II) with the substituted phenylamines of Formula (III) in a solution of di-isopropyl ethylamine and dimethylformamide results in the 2-oxo-propylamine compounds of Formula (I). Additional reaction with hydroxylamine (with or without alkyl substituents) results in the propanone oxime compounds of Formula (I).

Scheme 2 sets forth the approach that is used to obtain compounds of Formula (I) wherein A is C=O as defined above.

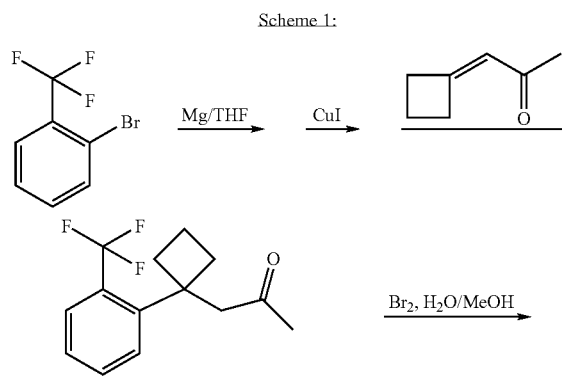

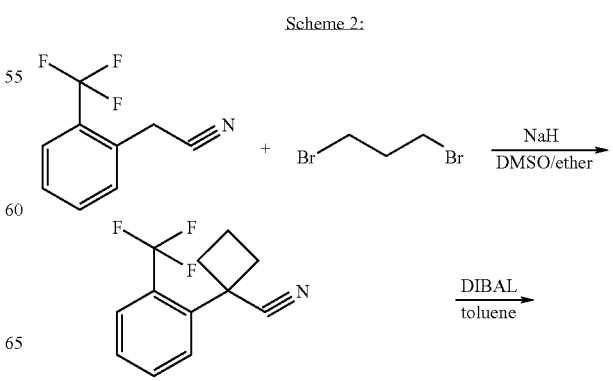

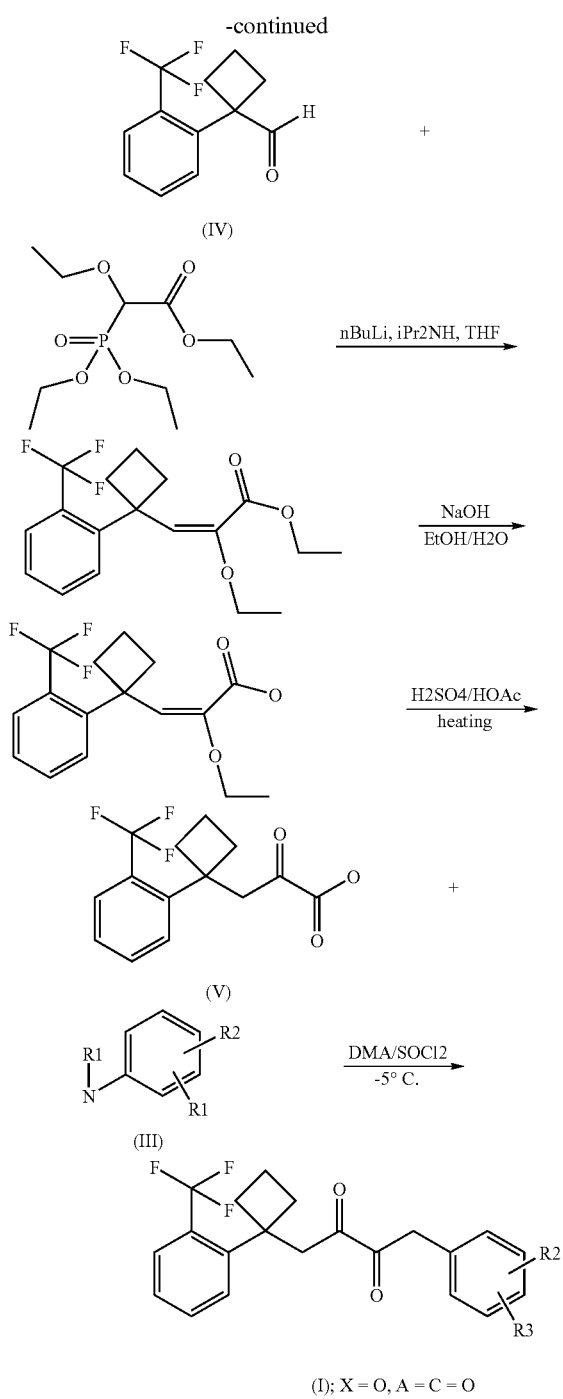

(I); X = O, A = C = O 2-trifluoromethyl-phenyl acetonitrile is mixed with 1,2-dibromopropane to produce the cyclobutanecarbonitrile compound, which is then reacted with diisobutylaluminum hydride in toluene resulting in the cyclobutanecarbaldehyde intermediate of Formula (IV). This intermediate is then mixed with diethoxy-phosphoryl-ethoxy-acetic acid ethyl ester, followed by two hydrolysis steps to produce 2-oxo-3-[1-2(trifluoromethyl-phenyl)-cyclobutyl-propionic acid of Formula (V). Finally, reaction with the phenylamines of Formula (III) in the presence of thionyl chloride and dimethyl acetamide results in the propionamide compounds of Formula (I).

Nomenclature

In general, the nomenclature used in this Application is based on AUTONOM™ v.4.0, a Beilstein Institute computerized system for the generation of IUPAC systematic nomenclature.

Chemical structures shown herein were prepared using ISIS® version 2.2. Any open valency appearing on a carbon, oxygen or nitrogen atom in the structures herein (other than substituent radicals) indicates the presence of a hydrogen.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, such as 1-100 mg daily, or 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction. A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about 1 mg of active ingredient or, more broadly, about 0.01 to about 100 mg, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about 1% to about 70% of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacyclo-heptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described in Examples 6-12.

EXAMPLES

The following preparations and examples are given to enable those skilled in the art to more clearly understand and to practice the present invention. They should not be considered as limiting the scope of the invention, but merely as being illustrative and representative thereof.

Example 1

4-Methyl-6-{2-oxo-3-[1-(2-trifluoromethyl-phenyl)-cyclobutyl]-propylamino}-benzo[d][1,2]oxazin-1-one Precursors 1-[1-(2-Trifluoromethyl-phenyl)-cyclobutyl]-propan-2-one A solution of 2-trifluoromethyl-phenylmagnesium bromide was prepared under nitrogen atmosphere from magnesium (1.02 g, 43 mmol) and 1-bromo-2-trifluoromethyl-benzene (10.31 g, 46 mmol) in tetrahydrofuran and cooled to −5° C. Cuprous iodide (3.53 g, 18.5 mmol) was added and the resulting mixture was stirred at −5° C. for 5 min, and then rapidly cooled to −70° C. 1-Cyclobutylidene-propan-2-one (1.2 g, 11 mmol) was added dropwise via a syringe to the mixture, which was then stirred for 1 h at −70° C. and allowed to warm to room temperature. The reaction mixture was poured into a saturated aqueous ammonium chloride solution and tetrahydrofuran was evaporated in a vacuum. The resulting residue was extracted with methylene chloride. The combined organic extracts were concentrated by evaporation in a vacuum. The residue was purified by column chromatography on silica gel utilizing a gradual increase in concentration of eluant (2%-10% ether-hexane) to yield 5.56 g of product.

$^1$H—NMR (CDCl$_3$), δ 7.63(dd, 1H), 7.45(t, 1H), 7.28(m, 2H), 3.05(s, 2H), 2.52(m, 4H), 2.08(m, 1H), 1.8(m, 1H), 1.68(s, 3H).

1-Bromo-3-[1-(2-trifluoromethyl-phenyl)-cyclobutyl]-propan-2-one

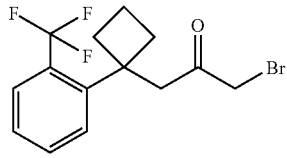

To an ice-cooled solution of 1-[1-(2-trifluoromethyl-phenyl)-cyclobutyl]-propan-2-one (2.56 g, 10 mmol) in MeOH (15 ml) was added Br$_2$ (0.5 ml, 10 mmol) slowly via a syringe. The reaction mixture was stirred for 15 min at 0° C., then 30 min at room temperature. To the reaction mixture was added H$_2$O (15 ml) and the mixture stirred for 15 min at room temperature. The reaction was monitored by TLC, and TLC showed no starting material left 15 min after addition of H$_2$O. The resulting solution was extracted twice with 25% n-hexane in EtOAc. The combined organic extracts were washed twice with saturated aqueous NaHCO$_3$ solution, dried over sodium sulfate and concentrated by evaporation in a vacuum. The residue was purified by column chromatography on silica-gel with 2% ether-hexane to yield 1.97 g of product.

$^1$H—NMR (CDCl$_3$), δ7.67(dd, 1H), 7.46(t, 1H), 7.32(t, 1H), 7.22(t, 1 H), 3.32(s, 2H), 3.27(s, 2H), 2.55(t, 4H), 2.12(m, 1H), 1.83(m, 1H).

4-Methyl-6-{2-oxo-3-[1-(2-trifluoromethyl-phenyl)-cyclobutyl]-propylamino}-benzo[d-1,2]oxazin-1-one

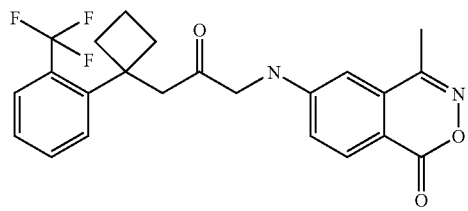

A solution of 0.35 g (1.04 mmol) of 1-bromo-3-[1-(2-trifluoromethyl-phenyl)-cyclobutyl]-propan-2-one, 0.184 g (1.04 mmol) of 6-amino-4-methyl-benzo[d][1,2]oxazin-1-one and 0.2 ml (1.1 mmol) of di-isopropyl ethylamine in 10 ml of DMF was heated at 80° C. overnight. The reaction mixture was partitioned between EtOAc and H$_2$O. The organic layer was separated, washed twice with H$_2$O, dried and concentrated by evaporation in a vacuum. The residue was purified by column chromatography on silica-gel (EtOAc-hexane 10% and 20%) to yield 26 mg of product.

$^1$H—NMR (CDCl$_3$), δ8.08(d, 1H), 7.67(dd, 1H), 7.38(dd, 1H), 7.28(d, 1H), 7.18(d, 1H), 6.71(dd, 1H), 6.33(d, 1H), 5.25(t, 1H), 3.46(b, 1H), 3.18(s, 2H), 2.59(m, 4H), 2.44(s, 3H), 2.14(m, 1H), 1.86(m, 1H).

MS (ei): M$^{(+)}$+H=431, M$^+$−H=429

Example 2

1-(4-Methyl-1-oxo-1H-benzo[d][1,2]oxazin-6-ylamino)-3-[1-(2-trifluoromethyl-phenyl)-cyclobutyl]propan-2-one oxime

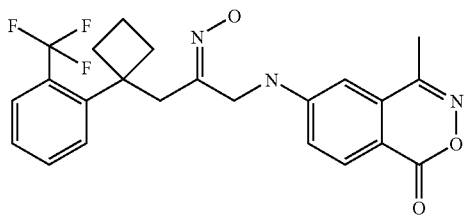

A solution of 29 mg of 4-methyl-6-{2-oxo-3-[1-(2-trifluoromethyl-phenyl)-cyclobutyl]-propylamino}-benzo[d][1,2]oxazin-1-one in EtOH (8 ml) was treated with 1 ml of 50% $NH_2OH$ HCl solution in $H_2O$ and NaOAc (15 mg). The solution was heated under reflux for 2 h and evaporated. The residue was purified by column chromatography on silica gel (10%-40% EtOAc-hexane) to yield 2 mg of product.

$^1$H—NMR (DMSO), δ7.85(dd, 1H), 7.6(m, 1H), 7.52(d, 1H), 7.32(tt, 1H), 7.23(dd, 1H), 6.92(dd, 2H), 3.69*(d, 2H), 3.42*(d, 2H), 2.78(s, 2H), 2.55(m, 4H), 2.37(s, 3H), 2.0(m, 1H), 1.75(m, 1H). * two peaks distinguishable for different rotamers, in 2:1 ratio.

MS (ei): $M^{(+)}$+H=446

Example 3

1-(3-Oxazol-5-yl-phenylamino)-3-[1-(2-trifluoromethyl-phenyl)-cyclobutyl]-propan-2-one oxime Precursors 4-Nitro-N-(3-oxazol-5-yl-phenyl)-benzenesulfonamide

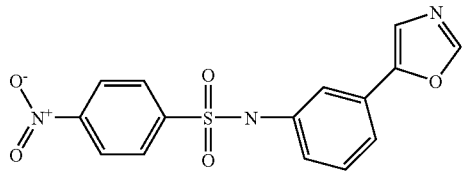

A solution of 3-oxazol-5-yl-phenylamine (0.5 g, 3.1 mmol) and 4-nitro-benzenesulfonyl chloride (0.91 g, 4.1 mmol) in pyridine (20 ml) was stirred over weekend at room temperature. The residue was partitioned between EtOAc and $H_2O$. The organic layer was separated, washed twice with $H_2O$ and once with saturated aqueous sodium chloride solution, dried and concentrated by evaporation. The residue was purified by column chromatography on silica-gel (5%-15% EtOAc-hexane) to afford 0.63 g of product.

$^1$H—NMR (DMSO), δ8.47(s, 1H), 8.39(d, 2H), 8.04(d, 2H), 7.67(s, 1H), 7.48(m, 2H), 7.38(t, 1H), 7.1(d, 1H)

MS (ei): $M^{(+)}$+H=346

1-Methanesulfonyl-4-nitro-benzene1-(3-oxazol-5-yl-phenylamino)-3-[1-(2-trifluoromethyl-phenyl)-cyclobutyl]-propan-2-one

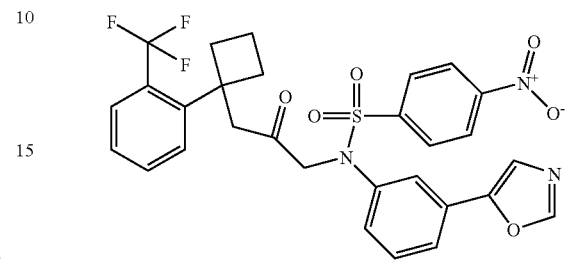

A solution of 0.14 g (0.41 mmol) of 4-nitro-N-(3-oxazol-5-yl-phenyl)-benzenesulfonamide in 2 ml DMF under nitrogen was stirred with NaH (15 mg of 60% oil dispersion, 0.39 mmol) at room temperature for 2 h. 0.15 g (0.045 mmol) of 1-bromo-3-[1-(2-trifluoromethyl-phenyl)-cyclobutyl]-propan-2-one was added. The mixture was stirred at room temperature overnight. The reaction mixture was partitioned between EtOAc and $H_2O$. The organic layer was separated, washed twice with $H_2O$, dried and concentrated by evaporation. The residue was purified by column chromatography on silica-gel (5%-20% EtOAc-hexane) to yield 162 mg of product as a white solid.

$^1$H—NMR ($CDCl_3$), δ8.25(d, 2H), 7.93(s, 1H), 7.71(d, 2H), 7.59(td, 1H), 7.53(dd, 1H), 7.32(m, 2H), 7.28(d, 1H), 7.03(m, 2H), 6.92(d, 2H), 3.9(b,2H), 3.03(s, 2H), 2.48(t, 4H), 2.08(m, 1H), 1.8(m, 1H).

MS (ei): $M^{(+)}$+H=600

1-(3-Oxazol-5-yl-phenylamino)-3-[1-(2-trifluoromethyl-phenyl)-cyclobutyl]-propan-2-one

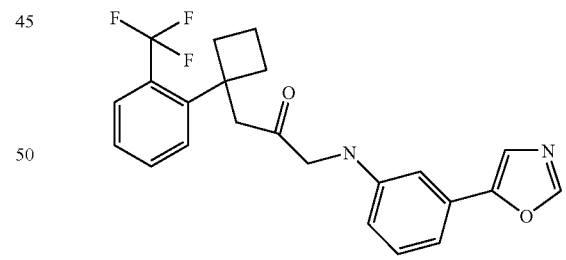

A mixture of 1-methanesulfonyl-4-nitro-benzene1-(3-oxazol-5-yl-phenylamino)-3-[1-(2-trifluoromethyl-phenyl)-cyclobutyl]-2 -one (160 mg, 0.27 mmol), PhSH (0.082 ml, 0.8 mmol), K2CO3 (149 mg, 1.08 mmol), MeCN (10 ml) and DMSO (0.25 ml) was heated to reflux for 30 min. The reaction mixture was partitioned between EtOAc and $H_2O$. The organic layer was separated, washed twice with $H_2O$, dried and concentrated by evaporation. The residue was purified by column chromatography on silica-gel (5%-15% EtOAc-hexane) to yield 43.7 mg of product.

¹H—NMR (CDCl₃), δ8.27(d, 1H), 7.66(d, 1H), 7.38(d, 1H), 7.2(m, 3H), 7.08(td, 1H), 6.79(t, 1H), 6.45(m, 2H), 4.52(t, 1H), 3.45(b, 2H), 3.13(s, 2H), 2.57(m, 4H), 2.14(m, 1H), 1.87(m, 1H).

MS (ei): M$^{(+)}$+H=415, M$^{(+)}$−H=413, 1-(3-Oxazol-5-yl-phenylamino)-3-[1-(2-trifluoromethyl-phenyl)-cyclobutyl]-propan-2-one oxime

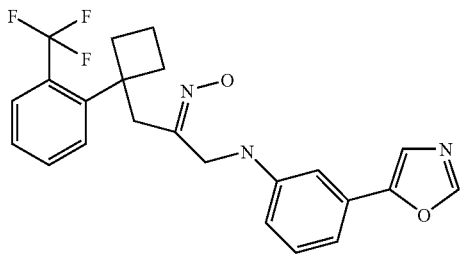

was obtained analogously to Example 1 from 1-(3-oxazol-5-yl-phenylamino)-3-[1-(2-trifluoromethyl-phenyl)-cyclobutl]-propan-2-one.

¹H—NMR (CDCl₃), δ7.88(s, 1H), 7.7(t, 1H), 7.05-7052 (m, 5H), 6.98(m, 1H), 6.67(m, 1H), 6.35(t, 1H), 3.46(b, 2H), 2.86(s, 2H), 2.57(m, 4H), 2.28(m, 1H), 2.08(m, 1H).

MS (ei): M$^{(+)}$+H=430

Example 4

1-(4-Oxazol-5-yl-phenylamino)-3-[1-(2-trifluoromethyl-phenyl)-cyclobutyl]-propan-2-one oxime Precursors 4-Nitro-N-(4-oxazol-5-yl-phenyl)-benzenesulfonamide

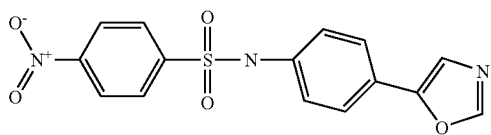

was obtained analogously to 4-nitro-N-(3-oxazol-5-yl-phenyl)-benzenesulfonamide with use of 4-oxazol-5-yl-phenylamine and 4-nitro-benzenesulfonyl chloride.

MS (ei): M$^{(+)}$+1=346

1-Methanesulfonyl-4-nitro-benzene 1-(4-oxazol-5-yl-phenylamino)-3-[1-(2-trifluoromethyl-phenyl)-cyclobutyl]-propan-2-one

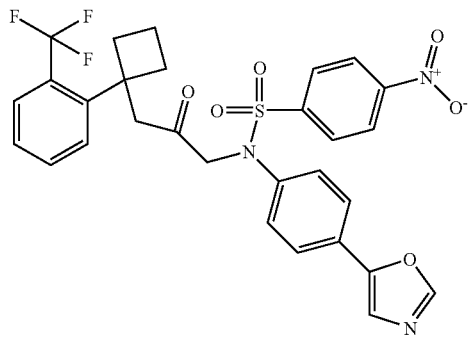

was obtained analogously to 1-methanesulfonyl-4-nitro-benzenel-(3-oxazol-5-yl-phenylamino)-3-[1 -(2-trifluoromethyl-phenyl)-cyclobutyl]-propan-2-one with use of 4-nitro-N-(4-oxazol-5-yl-phenyl)-benzenesulfonamide and 1-bromo-3-[1-(2-trifluoromethyl-phenyl)-cyclobutyl]-propan-2-one.

¹H—NMR (CDCl₃), δ8.24(d, 2H), 7.95(s, 1H), 7.69(d, 2H), 7.27-7.58(m, 4H), 6.93-7.18(m, 5H), 3.90(b, 2H), 3.04(s, 2H), 2.48(m, 4H), 2.10(m, 1H), 1.81(m, 1H).

MS (ei): M$^{(+)}$+H=600

1-(4-Oxazol-5-yl-phenylamino)-3-[1-(2-trifluoromethyl-phenyl)-cyclobutyl]-propan-2-one

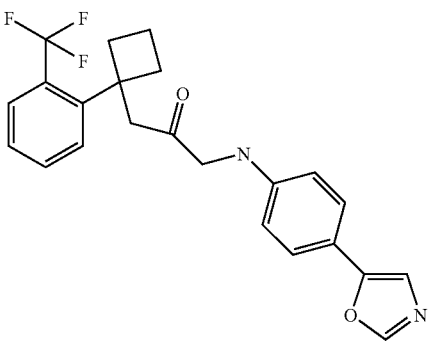

was obtained analogously to 1-(3-Oxazol-5-yl-phenylamino)-3-[1-(2-trifluoromethyl-phenyl)-cyclobutyl]-propan-2-one.

¹H—NMR (CDCl₃), δ7.81(s, 1H), 7.63(t, 1H), 7.5(m, 1H), 7.4(d, 2H), 7.1-7.3(m, 3H), 6.4(d, 2H), 4.53(b, 1H), 3.42(b, 2H), 3.12(s, 2H), 2.57(m, 4H), 2.13(m, 1H), 1.85(m, 1H).

MS (ei): M$^{(+)}$+H=415

1-(4-Oxazol-5-yl-phenylamino)-3-[1-(2-trifluoromethyl-phenyl)-cyclobutyl]-propan-2-one oxime

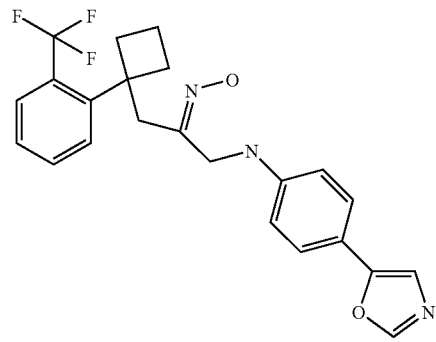

was obtained analogously to 1-(3-Oxazol-5-yl-phenylamino)-3-[1-(2-trifluoromethyl-phenyl)-cyclobutyl]-propan-2-one oxime.

$^1$H—NMR (CDCl$_3$), δ7.78(s, 1H), 7.68(t, 1H), 7.55(m, 1H), 7.45(m, 1H), 7.38(d, 2H), 7.32(m, 1H), 7.18(m, 1H), 6.37(d, 2H), 3.42(b, 1H), 3.15*(s, 2H), 2.82*(s, 2H), 2.52 (m, 4H), 2.22(m, 1H), 2.05(m, 1H), 1.81(m, 2H) *mixture of syn and anti, the ratio is about 1:1.

MS (ei): M$^{(+)}$+H=430

Example 5

N-(4-Oxazol-5-yl-phenyl)-2-oxo-3-[1-(2-trifluoromethyl-phenyl)-cyclobutyl]-propionamide Precursors 1-(2-Trifluoromethyl-phenyl)-cyclobutanecarbonitrile

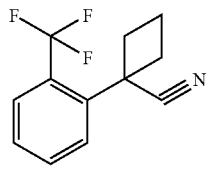

A solution of 12.6 g of (2-Trifluoromethyl-phenyl)-acetonitrile and 7.6 ml of 1,2-dibromopropane in 36 ml ether were added slowly through a dropping funnel to a suspension of 3.62 g of sodium hydride in 85 ml DMSO at 0° C. After addition, the ice-water bath was allowed to warm up to room temperature slowly and the reaction mixture was stirred at room temperature overnight. The reaction was carefully quenched with isopropyl and H$_2$O. The suspension became clear. The organic layer was separated, and the aqueous layer was extracted twice with ether. The combined organic extracts were combined, dried and concentrated by evaporation in a vacuum. The residue was purified by column chromatography on silica-gel (EtOAc-hexane 2%-4%) to yield 8.5 g of product as a white solid.

$^1$H—NMR (CDCl$_3$), δ7.72(dd, 1H), 7.58(t, 1H), 7.45(, 1H), 7.33(d, 1H) 2.92(m, 2H), 2.71(m, 2H), 2.54(m, 1H), 1.96(m, 1H).

1-(2-Trifluoromethyl-phenyl)-cyclobutanecarbaldehyde

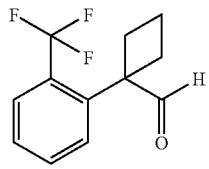

50.7 ml of diisobutylaluminum hydride was added dropwise over 2 hours to a solution of 8.5 g of 1-(2-trifluoromethyl-phenyl)-cyclobutanecarbonitrile in 85 ml toluene at 0° C. After addition, the ice-water bath was allowed to warm up to room temperature slowly and the reaction mixture was stirred at room temperature overnight. The reaction mixture was poured into 200 ml of 5% sulfuric acid in ice-water, and stirred for 10 minutes. The mixture was extracted four times with ether. The combined ether extracts were dried and concentrated by evaporation in a vacuum. The residue was purified by column chromatography on silica-gel (EtOAc-hexane 5%) to yield 6.2 g of product.

$^1$H—NMR (CDCl$_3$), δ9.7(s, 1H), 7.68(d, 1H), 7.57(t, 1H), 7.4(t, 1H), 7.27(d, 1H), 2.77(m, 2H), 2.62(m, 2H), 2.12(m, 1H), 1.87(m, 1H)

2-Ethoxy-3-[1-(2-trifluoromethyl-phenyl)-cyclobutyl]-acrylic acid ethyl ester

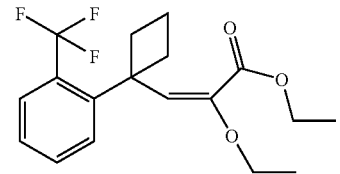

4.4 ml (11 mmol) n-butyllithium was added dropwise to a solution of 1.28 ml (9.2 mmol) of diisopropylamine in 25 ml tetrahydrofuran at 0° C. and stirred for 30 more minutes at 0° C. Then 1.97 g (7.4 mmol) of phosphonate, (diethoxyphosphoryl)-ethoxy-acetic acid ethyl ester was added dropwise and stirred for 20 more minutes at 0° C. 1.4 g (6.1 mmol) of 1-(2-trifluoro-methyl-phenyl)-cyclobutanecarbaldehyde in 5 ml tetrahydrofuran was added dropwise at 0° C. The ice-water bath was allowed to warm up to room temperature slowly and the reaction mixture was stirred at room temperature over the weekend. The reaction was quenched with saturated aqueous ammonium chloride. The resulting mixture was extracted with ethyl acetate. Ethyl acetate solution was washed with saturated aqueous sodium chloride solution, dried and concentrated by evaporation in a vacuum. The residue was purified by column chromatography on silica-gel (EtOAc-hexane 3%) to yield 0.61 g of product.

$^1$H—NMR (CDCl$_3$) δ6.93-7.61(m, 3H), 7.27(q, 1H), 6.75*(d, 1H), 5.77* (d, 1H)3.92(q, 2H), 3.79(q, 2H), 2.42-2.73(m, 4H), 2.07(m, 1H), 1.78(m, 1H)1.32(t, 3H), 1.11(t, 3H). *mixture of syn and anti, the ratio is about 2:1.

2-Ethoxy-3-[1-(2-trifluoromethyl-phenyl)-cyclobutyl]-acrylic acid

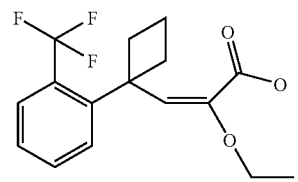

4.6 g of 2-Ethoxy-3-[1-(2-trifluoromethyl-phenyl)-cyclobutyl]-acrylic acid ethyl ester, 4.3 g of sodium hydroxide, 100 ml ethanol and 50 ml water (ethanol-water 2:1) were mixed and stirred for 2 hours at room temperature. Solvent was evaporated in vacuum, residue was distributed between water and ethyl acetate, and water solution was acidified with 1N hydrochloric acid, and extracted with ethyl acetate. The ethyl acetate extracts were washed with saturated aqueous sodium chloride solution, dried and concentrated by evaporation in a vacuum. 4.3 g of product was obtained and used for the next reaction without further purification.

¹H—NMR (CDCl₃), δ7.629 (d, 1H), 7.42(q, 1H), 7.28(q, 1H), 7.18(t, 1H), 6.87(b, 1H), 3.97(q, 2H), 2.55(m, 4H), 2.12(m, 1H), 1.85(m, 1H), 1.17(t, 3H).

2-Oxo-3-[1-(2-trifluoromethyl-phenyl)-cyclobutyl]-propionic acid

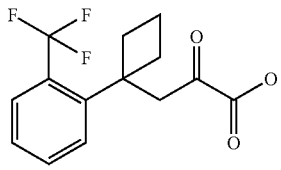

4.6 g of 2-Ethoxy-3-[1-(2-trifluoromethyl-phenyl)-cyclobutyl]-acrylic acid was stirred in 100 ml of 1M sulfuric acid and 15 ml of concentrated acetic acid overnight at 100° C. Water was added, extracted with ethyl acetate, and ethyl acetate solution was dried and concentrated by evaporation in a vacuum. The product (4.1 g) was obtained as a brown oil.

¹H—NMR (CDCl₃), δ7.62(d, 1H), 7.42(t, 1H), 7.3(d, 1H), 7.22(d, 1H), 3.56(s, 2H), 2.57(m, 4H), 2.15(m, 1H), 1.85(m, 1H).

MS (ei): M$^{(+)}$−H=285

N-(4-Oxazol-5-yl-phenyl)-2-oxo-3-[1-(2-trifluoromethyl-phenyl)-cyclobutyl]-propionamide

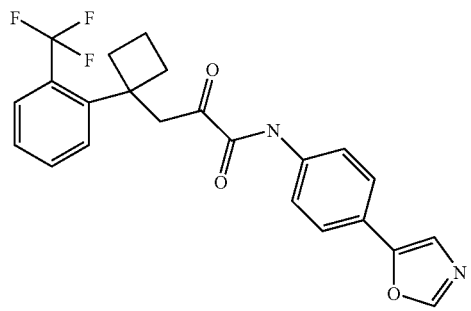

0.052 ml of thionyl chloride was added to a solution of 0.1 g of 2-Oxo-3-[1-(2-trifluoromethyl-phenyl)-cyclobutyl]-propionic acid in 2 ml of dimethyl acetamide at −5° C., and stirred for 30 min at −5° C. Then 56 mg of 4-oxazol-5-yl-phenylamine was added in solid form and stirred for 1 hour at room temperature. Potassium carbonate was added and stirred overnight at room temperature. The reaction was quenched with water and extracted with ethyl acetate. The combined ethyl acetate extracts were washed twice with water, dried and concentrated by evaporation. The residue was purified by column chromatography on silica-gel (EtOAc-hexane 10%-20%) to yield 63 mg of product.

¹H—NMR (CDCl₃), δ7.83(d, 2H), 7.62(s, 1H), 7.15(s, 1H), 6.77(d, 2H), 3.92(b, 2H).

MS (ei): M$^{(+)}$+H=161

Example 6

N-(3-Isoxazol-5-yl-phenyl)-2-oxo-3-[1-(2-trifluoromethyl-phenyl)-cyclobutyl]-propionamide

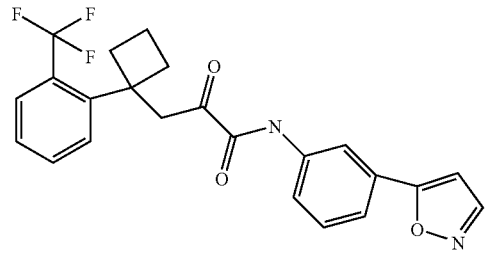

was obtained analogously to N-(4-oxazol-5-yl-phenyl)-2-oxo-3-[1-(2-trifluoromethyl-phenyl)-cyclobutyl]propionamide with use of 2-oxo-3-[1-(2-trifluoromethyl-phenyl)-cyclobutyl]-propionic acid and 3-isoxazol-5-yl-phenylamine.

¹H—NMR (CDCl₃) δ8.62(s, 1H), 8.0(d, 2H), 7.7(s, 1H), 7.6(m, 3H), 7.39(t, 1H), 7.27(m, 2H), 3.68(s, 2H), 2.58(m, 4H), 2.16(m, 1H), 1.86(m, 1H).

MS (ei): M$^{(+)}$+H=429, M$^+$−H=427

Example 7

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt/wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5% active compound are prepared as nasal spray formulations. The formulations optionally contain inactive ingredients such as, for example, microcrystalline cellulose, sodium carboxymethylcellulose, dextrose, and the like. Hydrochloric acid or sodium hydroxide may be added to adjust pH. The nasal spray formulations may be delivered via a nasal spray metered pump typically delivering about 50-100 µL of formulation per actuation. A typical dosing schedule is 2-4 sprays every 4-12 hours.

Example 8

Glucocorticoid Receptor Binding Assay

The affinity of glucocorticoid receptor antagonists for the glucocorticoid receptor was determined in competitive binding assays by the ability of the antagonist to compete with tritiated dexamethasone.

All assay steps were performed on ice in 96-well plates. Binding buffer contained 10 mM potassium phosphate pH 7.4, 20 mM $Na_2Mo_4$, 100 µM EDTA, 2% DMSO, and 5 mM DTT. Human recombinant purified glucocorticoid receptor was used at 1 nM. Compounds tested had up to 2% DMSO final concentration. Non-specific binding condition was 1 µM dexamethasone. The radioligand used for the competition assay was 2 nM $^3$H-Dexamethasone (83 Ci/mmol stock solution). Buffer, compounds or vehicles, GR, and radioligand were incubated at 4° C. overnight. Unifilter GF/B 96-well filter plates were treated with 0.5% PEI after incubation. Samples were transferred to filter plates by a cell harvester. Filter plates were washed five times with 50 mM Tris pH 7.5 and 5 mM EDTA wash buffer. Samples were dried at 65° C. for about 1 hr. Scintillation fluid was added to filter plates at 50 µL/ well and $^3$H cpm were measured on the TopCount scintillation counter. Results of the binding assay of several compounds from the present invention are shown in Table 1.

TABLE 1

| Compound | Binding Affinity Ki (µM) |
| --- | --- |
| Example 2 | 0.089 |
| Example 1 | 0.405 |
| Example 5 | 0.723 |
| Example 4 | 0.851 |
| Example 3 | 2.102 |
| Example 6 | 2.398 |

Example 9

Transrepression Activity: Inhibition of Cytokine Production in LPS-stimulated Human Peripheral Blood Mononuclear Cells Blood is collected from healthy human volunteers by venipuncture into heparinized tubes. Blood is diluted 1:1 with Dulbecco's phosphate-buffered saline (PBS) and layered over Histopaque-1.077 in 50 ml centrifuge tubes. Tubes are centrifuged at 800×g for 25 minutes at room temperature. Mononuclear cells at the plasma/Histopaque interface are collected, washed three times with PBS, and resuspended at $1\times10^6$ cells/ml in RPMI 1640 medium supplemented with 10% fetal bovine serum (FBS) and 100 units/ml penicillin/100 µg/ml streptomycin. Aliquots (250 µl) of this cell suspension are pre-incubated with compounds at various dilutions (final DMSO concentration is 0.5%) in sterile polypropylene plates for 30 minutes at 37° C., 5% $CO_2$. LPS is added to 1 ng/ml and the plates are returned to the incubator for an additional three hours. Aliquots of the medium are removed and frozen at −80° C. Cytokine levels (TNFα, IL6 and IL8) in these samples are determined using the BD-Pharmingen OptEIA kits according to the manufacturer's instructions. The IC50 is defined as the concentration of compound which decreases the cytokine production in response to 1 ng/ml LPS to 50% of that in control wells without RO compounds.

Example 10

Transactivation Activity: Tyrosine Aminotransferase Activity in Rat Liver Cells

H4IIE rat hepatoma cells are plated ($4\times10^5$ cells/ml in a 24 well plate) in cDMEM supplemented with 10% FBS and incubated for 24 hours at 37° C., 5% $CO_2$ Compounds at various dilutions (final DMSO concentration is 0.5%) are added and the plates are incubated for an additional 24 hours. The medium is removed, the cell monolayer is washed carefully once with PBS, and 0.2 ml cell lysis buffer (10 mM Tris pH 7.5, 10 mM EDTA, 0.25M sucrose) is added. Plates can be stored at −70° C. Cells are lysed by freezing and thawing 3 times; lysates are clarified by centrifugation for 5 min. 40 µl/well p-hydroxybenzaldehyde as standard, buffer control, or aliquots of lysate are added to a clear 96 well plate. 20 µl/well TAT buffer (50 mM $KH_2PO_4$ pH 7.6, 5 mg/ml BSA, 1 mM EDTA, 0.1 mM DTT) is added, followed by 140 µl/well assay mix (8.2 mM tyrosine solution, 0.125 M $KH_2PO_4$, 20 mM a-ketoglutarate, 0.3 mM pyridoxal 5-phosphate). Reactions are incubated at 37° C. for 15 min, and terminated by the addition of 20 µl/well 7 N KOH, followed by incubation at 37° C. in the dark for 30 min. Product formation is monitored by absorbance at 340 nm, and is expressed as nmoles/min/mg protein, as calculated from the p-hydroxybenzaldehyde standard curve. EC50 for each compound is defined as the concentration of compound resulting in 50% of the maximum TAT induction for that compound.

The invention claimed is:
1. A compound of formula I

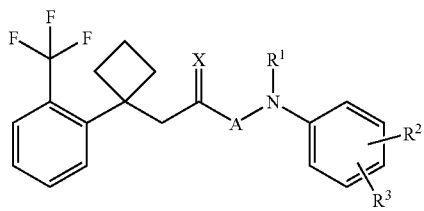

(I)

wherein:
A is $CH_2$ or C=O
$R^1$ is H or $C_1$-$C_6$ alkyl;
$R^2$ and $R^3$ are each independently H, $CF_3$, $NO_2$ or an optionally substituted five-membered heteroaryl ring;
or $R^2$ and $R^3$ together form an oxazolinyl ring substituted with 0-2 substituents selected from the group consisting of $C_1$-$C_6$ alkyl and oxo, with the proviso that when $R^2$ and $R^3$ together form said oxazolinyl or oxazinyl ring, A is $CH_2$;
X is O or N—$OR^4$, wherein $R^4$ is H or $C_1$-$C_6$ alkyl;
and pharmaceutically acceptable salts thereof.

2. The compound according to claim 1, wherein A is $CH_2$ and $R^1$ is H.

3. The compound according to claim 2, wherein $R^2$ is selected from the group consisting of oxazolyl, isoxazolyl, oxadiazolyl and tetrazolyl.

4. The compound according to claim 1, selected from the group consisting of
6-{2-Hydroxyimino-3-[1-(2-trifluoromethyl-phenyl)-cyclobutyl]-propylamino}-4-methyl-benzo[d][1,2]oxazin-1-one;
4-Methyl-6-{2-oxo-3-[1-(2-trifluoromethyl-phenyl)-cyclobutyl]-propylamino}-benzo[d][1,2]oxazin-1-one;
1-(4-Isoxazol-5-yl-phenylamino)-3-[1-(2-trifluoromethyl-phenyl)-cyclobutyl]-propan-2-one oxime;
1-(3-Isoxazol-5-yl-phenylamino)-3-[1-(2-trifluoromethyl-phenyl)-cyclobutyl]-propan-2-one oxime;
1-(3-Oxazol-5-yl-phenylamino)-3-[1-(2-trifluoromethyl-phenyl)-cyclobutyl]-propan-2-one oxime;
1-[3-(1H-Tetrazol-5-yl)-phenylamino]-3-[1-(2-trifluoromethyl-phenyl)-cyclobutyl]-propan-2-one oxime;
1-(4-Oxazol-5-yl-phenylamino)-3-[1-(2-trifluoromethyl-phenyl)-cyclobutyl]-propan-2-one oxime;
2-Ethoxyimino-N-(4-oxazol-5-yl-phenyl)-3-[1-(2-trifluoromethyl-phenyl)-cyclobutyl]-propionamide;
N-(4-Isoxazol-5-yl-phenyl)-2-oxo-3-[1-(2-trifluoromethyl-phenyl)-cyclobutyl]-propionamide;
N-(3-Isoxazol-5-yl-phenyl)-2-oxo-3-[1-(2-trifluoromethyl-phenyl)-cyclobutyl]-propionamide; and
N-(4-Oxazol-5-yl-phenyl)-2-oxo-3-[1-(2-trifluoromethyl-phenyl)-cyclobutyl]-propionamide.

5. A method of treating an inflammatory disease through modulation of a glucocorticoid receptor, wherein said inflammatory disease is asthma, rheumatoid arthritis, allergic diseases, and graft-versus-host diseases, comprising administering to a subject in need thereof a compound of formula I:

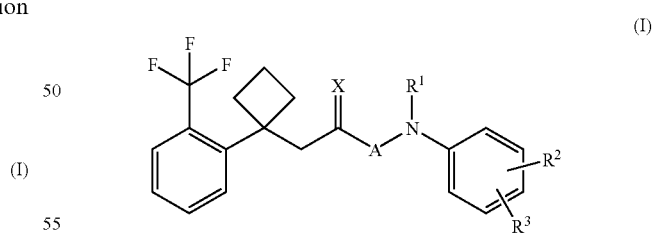

(I)

wherein:
A is $CH_2$ or C=O
$R^1$ is H or $C_1$-$C_6$ alkyl;
$R^2$ and $R^3$ are each independently H, $CF_3$, $NO_2$ or an optionally substituted five-membered heteroaryl ring;
or $R^2$ and $R^3$ together form an oxazolinyl or oxazinyl ring substituted with 0-2 substituents selected from the group consisting of $C_1$-$C_6$ alkyl and oxo, with the proviso that when $R^2$ and $R^3$ together form said oxazolinyl ring, A is $CH_2$;

X is O or N—OR⁴, wherein R⁴ is H or $C_1$-$C_6$ alkyl;
and pharmaceutically acceptable salts thereof.

6. The method of claim 5 wherein A is $CH_2$ and $R^1$ is H.

7. The method of claim 6 wherein $R^2$ is selected from the group consisting of oxazolyl, isoxazolyl, oxadiazolyl and tetrazolyl.

8. The method of claim 6 wherein the compound is selected from the group consisting of
- 6-{2-Hydroxyimino-3-[1-(2-trifluoromethyl-phenyl)-cyclobutyl]-propylamino}-4-methyl-benzo[d][1,2]oxazin-1one;
- 4-Methyl-6-{2-oxo-3-[1-(2-trifluoromethyl-phenyl)-cyclobutyl]-propylamino}-benzo [d][1,2]oxazin-1-one;
- 1-(4-Isoxazol-5-yl-phenylamino)-3-[1-(2-trifluoromethyl-phenyl)-cyclobutyl]-propan-2-one oxime;
- 1-(3-Isoxazol-5-yl-phenylamino)-3-[1-(2-trifluoromethyl-phenyl)-cyclobutyl]-propan-2-one oxime;
- 1-(3-Oxazol-5-yl-phenylamino)-3-[1-(2-trifluoromethyl-phenyl)-cyclobutyl]-propan-2-one oxime;
- 1-[3-(1H-Tetrazol-5-yl)-phenylamino]-3-[1-(2-trifluoromethyl-phenyl)-cyclobutyl]-2-one oxime;
- 1-(4-Oxazol-5-yl-phenylamino)-3-[1-(2-trifluoromethyl-phenyl)-cyclobutyl]-propan-2-one oxime;
- 2-Ethoxyimino-N-(4-oxazol-5-yl-pheny;)-3-[1-(2-trifluoromethyl-phenyl)-cyclobutyl]-propionamide;
- N-(4-Isoxazol-5-yl-phenyl)-2-oxo-3-[1-(2-trifluoromethyl-phenyl)-cyclobutyl]-propionamide;
- N-(3-Isoxazol-5-yl-phenyl)-2-oxo-3-[1-(2-trifluoromethyl-phenyl)-cyclobutyl]-propionamide; and
- N-(4-Oxazol-5-yl-phenyl)-2-oxo-3-[1-(2-trifluoromethyl-phenyl)-cyclobutyl]-propionamide.

9. A pharmaceutical composition comprising: an effective amount of a compound of Formula I;

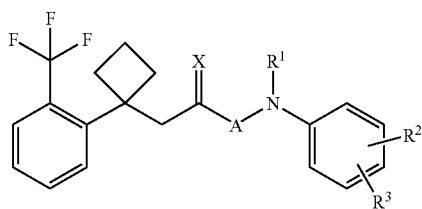

(I)

wherein:
A is $CH_2$ or C=O
$R^1$ is H or $C_1$-$C_6$ alkyl;
$R^2$ and $R^3$ are each independently H, $CF_3$, $NO_2$ or an optionally substituted five-membered heteroaryl ring;
or $R^2$ and $R^3$ together form an oxazolinyl or oxazinyl ring substituted with 0-2 substituents selected from the group consisting of $C_1$-$C_6$ alkyl and oxo, with the proviso that when $R^2$ and $R^3$ together form said oxazolinyl ring, A is $CH_2$;
X is O or N—OR⁴, wherein R⁴ is H or $C_1$-$C_6$ alkyl;
and pharmaceutically acceptable salts thereof; and
a pharmaceutically acceptable excipient.

10. The pharmaceutical composition of claim 9, wherein A is $CH_2$ and $R^1$ is H.

11. The pharmaceutical composition of claim 10, wherein $R^2$ is selected from the group consisting of oxazolyl, isoxazolyl, oxadiazolyl and tetrazolyl.

12. The pharmaceutical composition of claim 10, selected from the group consisting of
- 6-{2-Hydroxyimino-3-[1-(2-trifluoromethyl-phenyl)-cyclobutyl]-propylamino}-4-methyl-benzo[d][1,2]oxazin-1one;
- 4-Methyl-6-{2-oxo-3-[1-(2-trifluoromethyl-phenyl)-cyclobutyl]-propylamino}-benzo[d][1,2]oxazin-1-one;
- 1-(4-Isoxazol-5-yl-phenylamino)-3-[1-(2-trifluoromethyl-phenyl)-cyclobutyl]-propan-2-one oxime;
- 1-(3-Isoxazol-5-yl-phenylamino)-3-[1-(2-trifluoromethyl-phenyl)-cyclobutyl]-propan-2-one oxime;
- 1-(3-Oxazol-5-yl-phenylamino)-3-[1-(2-trifluoromethyl-phenyl)-cyclobutyl]-propan-2-one oxime;
- 1-[3-(1H-Tetrazol-5-yl)-phenylamino]-3-[1-(2-trifluoromethyl-phenyl)-cyclobutyl]-propan-2-one oxime;
- 1-(4-Oxazol-5-yl-phenylamino)-3-[1-(2-trifluoromethyl-phenyl)-cyclobutyl]-propan-2-one oxime;
- 2-Ethoxyimino-N-(4-oxazol-5-yl-phenyl)-3-[1 -(2-trifluoromethyl-phenyl)-cyclobutyl]-propionamide;
- N-(4-Isoxazol-5-yl-phenyl)-2-oxo-3-[1 -(2-trifluoromethyl-phenyl)-cyclobutyl]-propionamide;
- N-(3-Isoxazol-5-yl-phenyl)-2-oxo-3-[1-(2-trifluoromethyl-phenyl)-cyclobutyl]-propionamide; and
- N-(4-Oxazol-5-yl-phenyl)-2-oxo-3-[1-(2-trifluoromethyl-phenyl)-cyclobutyl]-propionamide.

13. The method of claim 5, wherein said inflammatory disease is asthma or rheumatoid arthritis.

\* \* \* \* \*